US006570006B1

(12) United States Patent
Whitfield et al.

(10) Patent No.: US 6,570,006 B1
(45) Date of Patent: May 27, 2003

(54) BACTERIAL GENE AND METHOD OF TREATING A GRAM NEGATIVE BACTERIAL INFECTION

(75) Inventors: Chris Whitfield, Guelph (CA); Jeremy A. Yethon, Guelph (CA); David E. Heinrichs, Guelph (CA)

(73) Assignee: University of Guelph, Guelph (CA)

( * ) Notice: Subject to any disclaimer, the term of this patent is extended or adjusted under 35 U.S.C. 154(b) by 0 days.

(21) Appl. No.: 09/719,155

(22) PCT Filed: Jun. 11, 1999

(86) PCT No.: PCT/CA99/00545

§ 371 (c)(1), (2), (4) Date: Jun. 29, 2001

(87) PCT Pub. No.: WO99/66049

PCT Pub. Date: Dec. 23, 1999

Related U.S. Application Data

(60) Provisional application No. 60/089,189, filed on Jun. 12, 1998, and provisional application No. 60/096,026, filed on Aug. 10, 1998.

(51) Int. Cl.$^7$ ........................ C07H 21/04; A01N 43/04; A61K 31/70

(52) U.S. Cl. ........................................ 536/23.7; 514/44

(58) Field of Search ............................... 435/91.1, 69.8, 435/252.3, 194, 252.8, 320.1; 536/23.7, 24.32; 424/200.1

(56) References Cited

U.S. PATENT DOCUMENTS

| | | | | |
|---|---|---|---|---|
| 5,110,588 A | * | 5/1992 | Morona et al. | 424/200.1 |
| 5,573,935 A | * | 11/1996 | Beeler et al. | 435/194 |
| 6,406,841 B1 | * | 6/2002 | Lee et al. | 435/5 |

FOREIGN PATENT DOCUMENTS

| | | |
|---|---|---|
| WO | WO 98/50557 | 11/1998 |

OTHER PUBLICATIONS

Watson et al., Recombinant DNA Second Edition, Scientific American Books, 1992.*

Klena et al., THe rfaS Gene, WHich is Involved in Production of a Rough FOrm of Lipopolysaccharide Core in *Escherichia coli* K–12, Is Not Present in the rfa Cluster of *Salmonella typhimurium* LT2, J. Bacteriology, 175(5), 1524–1527 (1993).*

Parker, C.T. et al., J. of Bacteriology, vol. 3, No. 174, p. 930–934, XP002072854 (1992).

Heinrichs, D.E. et al. J. Biol. Chem., vol. 273, No. 15, p. 8849–8859, XP002118872 (1998).

Walsh, A.G. et al., Abstracts of the General Meeting of the American Society For Microbiology, p. 65, XP002072856 (1997).

Mamat, U. et al., Molecular Microbiol., vol. 15, No. 6, pp. 1115–1125, XP000857877 (1995).

Goldman, R. et al. Nature, vol. 329, p. 162–164, XP002126442, (1987).

Heinrichs et al. GenBank Accession No. AF0197545.

Heinrichs, D.E. et al., Mol. Microbiol., vol. 30, No. 2, p. 221–232, XP002118873 (1998).

Heinrichs, D.E., J. Biol. Chem., vol. 273, No. 45, p. 29497–29505, XP002118874 (1998).

Yethon, J. et al., J. Biol. Chem., vol. 273, No. 41, p. 26310–26316, XP002118875 (1998).

Walsh, A.G. et al. Mol. Microbiol. vol. 35, No. 4, p. 718–727, (2000).

Yethon, J.A. et al. J. Biol. Chem., vol. 276, No. 8, p. 5498–5504 (2001).

Yethon et al. J. Bacteriol., vol. 182, No. 19, 5620–5623, (2000).

Yethon et al. Infect. Immun., vol. 68, No. 8, p. 4485–4491, (2000).

* cited by examiner

*Primary Examiner*—James Housel
*Assistant Examiner*—Zachariah Lucas
(74) *Attorney, Agent, or Firm*—Bereskin & Parr

(57) ABSTRACT

Described are a novel gene (waaP) and a protein (WaaP) which has an enzymatic activity that is involved in heptose modification in the lipopolysaccharide of bacterial membranes. Also described is a method and series of compounds which are active against bacterial pathogens wherein the method comprises the administration of sufficient amount of an inhibitor of WaaP protein activity in gram negative bacteria.

2 Claims, 9 Drawing Sheets

FIGURE 4

```
LOCUS       R1RFAP     795 BP DS-DNA

BASE COUNT      209 A    172 C    207 G    207 T      0 OTHER
ORIGIN
  1 ATGGTTGAAC TTAAAGAGCC GTTTGCCACG TTATGGCGCG GCAAAGATCC TTTTGAGGAA
 61 GTTAAAACCT TGCAGGGTGA GGTATTTCGT GAACTGGAAA CTCGCCGTAC TCTGCGCTTT
121 GAAATGGCGG GCAAAAGCTA TTTTCTCAAA TGGCATCGCG GCACGACCCT GAAAGAGATA
181 ATCAAAAATT TACTCTCATT GCGGATGCCA GTATTAGGCG CTGACCGCGA ATGGAATGCG
241 ATTCATCGAC TGCGGGATGT CGGCGTTGAT ACTATGTATG GGGTGGCATT TGGCGAAAAA
301 GGCATGAATC CGCTGACCAG AACTTCATTT ATTATTACCG AAGATCTGAC ACCAACCATA
361 AGTCTGGAAG ATTACTGTGC TGACTGGGCG ACTAACCCTC CAGATGTTCG CGTAAAGCGT
421 ATGCTTATTA AGCGTGTCGC GACGATGGTG CGCGATATGC ATGCTGCGGG CATTAACCAC
481 CGTGACTGTT ATATCTGTCA TTTCCTGCTG CACTTGCCTT TTTCCGGTAA GGAAGAGGAG
541 TTAAAAATTT CGGTAATTGA CCTGCACCGG GCGCAGCTTC GCACGCGCGT TCCACGTCGT
601 TGGCGGGATA AAGATCTTAT TGGGCTTTAT TTTTCTTCGA TGAATATCGG CCTGACTCAG
661 CGGGATATCT GGCGGTTTAT GAAAGTGTAT TTTGCCGCCC CGCTTAAAGA CATTCTCAAG
721 CAGGAACAAG GACTGCTGTC GCAAGCAGAA GCAAAAGCCA CAAAAATCAG GGAAAGAACG
781 ATTCGAAAAT CGTTG
```

FIGURE 5

```
LOCUS       RFAP R1       265 AA    PROT

    Peptide       1      265     1 to 795 of R1rfaP (translated)
ORIGIN
        1 MVELKEPFAT LWRGKDPFEE VKTLQGEVFR ELETRRTLRF EMAGKSYFLK WHRGTTLKEI
       61 IKNLLSLRMP VLGADREWNA IHRLRDVGVD TMYGVAFGEK GMNPLTRTSF IITEDLTPTI
      121 SLEDYCADWA TNPPDVRVKR MLIKRVATMV RDMHAAGINH RDCYICHFLL HLPFSGKEEE
      181 LKISVIDLHR AQLRTRVPRR WRDKDLIGLY FSSMNIGLTQ RDIWRFMKVY FAAPLKDILK
      241 QEQGLLSQAE AKATKIRERT IRKSL
```

FIGURE 6

```
LOCUS       R3 RFAP       795 BP DS-DNA

BASE COUNT      210 A    172 C    206 G    207 T      0 OTHER
ORIGIN
       1 ATGGTTGAAC TTAAAGAGCC GTTTGCCACG TTATGGCGCG GCAAAGATCC TTTTGAGGAA
      61 GTTAAAACCT TGCAGGGTGA GGTATTTCGT GAACTGGAAA CTCGCCGTAC TCTGCGCTTT
     121 GAAATGGCGG GCAAAAGCTA TTTTCTCAAA TGGCATCGCG GCACGACCCT GAAAGAGATA
     181 ATCAAAAATT TACTCTCATT GCGGATGCCA GTATTAGGCG CTGACCGCGA ATGGAATGCG
     241 ATTCATCGAC TGCGGGATGT CGGCGTTGAT ACTATGTATG GGGTGGCATT TGGCGAAAAA
     301 GGCATGAATC CGCTGACCAG AACTTCATTT ATTATTACCG AAGATCTGAC ACCAACCATA
     361 AGTCTTGAAG ATTACAGTGC TGACTGGGCG ACTAACCCTC CAGATGTTCG CGTAAAGCGT
     421 ATGCTTATTA AGCGTGTCGC GACGATGGTG CGCGATATGC ATGCTGCGGG CATTAACCAC
     481 CGTGACTGTT ATATCTGTCA TTTCCTGCTG CACTTGCCTT TTTCCGGTAA GGAAGAGGAG
     541 TTAAAAATTT CGGTAATTGA CCTGCACCGG GCGCAGCTTC GCACGCGCGT TCCACGTCGT
     601 TGGCGGGATA AAGATCTTAT TGGGCTTTAT TTTTCTTCGA TGAATATCGG CCTGACTCAG
     661 CGGGATATCT GGCGGTTTAT GAAAGTGTAT TTTGCCGCCC CGCTTAAAGA CATTCTCAAG
     721 CAGGAACAAG GACTGCTGTC GCAAGCAGAA GCAAAAGCCA CAAAAATCAG GGAAAGAACG
     781 ATTCGAAAAT CGTTG
```

FIGURE 7

```
LOCUS       RFAP R3       265 AA     PROT

FEATURES        From  To/Span     Description
    Peptide       1      265      1 to 795 of R3 rfaP (translated)
ORIGIN
        1 MVELKEPFAT LWRGKDPFEE VKTLQGEVFR ELETRRTLRF EMAGKSYFLK WHRGTTLKEI
       61 IKNLLSLRMP VLGADREWNA IHRLRDVGVD TMYGVAFGEK GMNPLTRTSF IITEDLTPTI
      121 SLEDYSADWA TNPPDVRVKR MLIKRVATMV RDMHAAGINH RDCYICHFLL HLPFSGKEEE
      181 LKISVIDLHR AQLRTRVPRR WRDKDLIGLY FSSMNIGLTQ RDIWRFMKVY FAAPLKDILK
      241 QEQGLLSQAE AKATKIRERT IRKSL
```

FIGURE 8

```
LOCUS        R4RFAP        795 BP DS-DNA

FEATURES         From  To/Span      Description
    frag          795        1 (C)  6854 to 7648 of F2513rfaC-kdtA
BASE COUNT        212 A    177 C     204 G     202 T       0 OTHER
ORIGIN
          1 ATGGTTGAAC TTAAAGAGCC GTTTGCCACG TTATGGCGCG GTAAAGATCC TTTTGAGGAA
         61 GTTAAAACCT TGCAGGGTGA GGTATTTCGT GAACTGGAAA CTCGCCGCAC TCTGCGCTTT
        121 GAAATGGCGG GCAAAAGCTA TTTTCTCAAA TGGCATCGCG GCACGACCCT GAAAGAGATA
        181 ATCAAAAATT TACTCTCATT GCGGATGCCA GTATTAGGCG CAGACCGCGA ATGGAATGCG
        241 ATTCATCGAC TGCGGGATGT CGGCGTTGAT ACTATGTATG GGGTGGCATT CGGCGAAAAA
        301 GGCATTAATC CGCTCACCAG AACCTCGTTT ATTATAACCG AAGATCTGAC ACCAACCATC
        361 AGTCTGGAAG ATTACTGTGC TGACTGGGCG ACTAACCCAC CAGATGTTCG CGTAAAGCGT
        421 ATGCTTATTA AGCGTGTCGC GACGATGGTG CGCGATATGC ATGCTGCGGG CATTAACCAC
        481 CGCGACTGTT ATATCTGTCA TTTCCTGCTA CACTTGCCTT TTTCCGGTAA GGAAGAGGAG
        541 TTAAAAATTT CGGTAATTGA CCTGCACCGG GCGCAGCTTC GCACGCGCGT TCCACGTCGT
        601 TGGCGCGATA AAGATCTTAT TGGGCTTTAT TTTTCTTCGA TGAATATCGG CCTGACTCAG
        661 CGGGATATCT GGCGGTTTAT GAAAGTGTAT TTTGCCGCCC CGCTTAAAGA CATTCTCAAG
        721 CAGGAACAAG GACTGCTGTC GCAAGCAGAA GAAAAAGCCA CAAAAATCAG GGAAAGAACG
        781 ATTCGAAAAT CGTTG
```

FIGURE 9

```
LOCUS       RFAPR4        265 AA     PROT

FEATURES         From  To/Span      Description
    Peptide        1      265       1 to 795 of R4rfaP (translated)
ORIGIN
        1 MVELKEPFAT LWRGKDPFEE VKTLQGEVFR ELETRRTLRF EMAGKSYFLK WHRGTTLKEI
       61 IKNLLSLRMP VLGADREWNA IHRLRDVGVD TMYGVAFGEK GINPLTRTSF IITEDLTPTI
      121 SLEDYCADWA TNPPDVRVKR MLIKRVATMV RDMHAAGINH RDCYICHFLL HLPFSGKEEE
      181 LKISVIDLHR AQLRTRVPRR WRDKDLIGLY FSSMNIGLTQ RDIWRFMKVY FAAPLKDILK
      241 QEQGLLSQAE EKATKIRERT IRKSL
```

BACTERIAL GENE AND METHOD OF TREATING A GRAM NEGATIVE BACTERIAL INFECTION

FIELD OF THE INVENTION

The invention relates to a novel gene, waaP, which is involved in heptose modification in the lipopolysaccharide of bacterial membranes, its corresponding protein, WaaP, and a method of preventing or treating gram negative bacterial infections, particularly attenuating virulent gram negative pathogens including compounds for such attenuation.

BACKGROUND OF THE INVENTION

The outer membrane of Gram-negative bacteria is a barrier to many antibiotics and host defense factors (Vaara, M., 1992). The outer leaflet of this membrane is comprised almost exclusively of lipopolysaccharide (LPS), a unique glycolipid with structural features essential to outer membrane stability. In *Escherichia coli* and *Salmonella enterica*, the LPS molecule is conceptually divided into three distinct regions: 1) a hydrophobic membrane anchor designated lipid A; 2) a short chain of sugar residues with multiple phosphoryl substituents, referred to as the core oligosaccharide (core OS); and 3) a structurally diverse polymer composed of oligosaccharide repeats, termed the O antigen. Lipid A and the core OS are synthesized together as a single unit (lipid A-core, FIG. 1), which serves as an acceptor for preformed O antigen to yield the completed LPS molecule (Whitfield, C. et al., 1997; Raetz, C. R. H. 1996).

Five distinct core OS structures have been identified in *E. coli* (core types K-12, R1, R2, R3, and R4), and two more are known for *S. entarica* (Holst, 0. and Brade, H., 1992; Olsthoorn, M. M. A., et al. 1998). The genes responsible for biosynthesis of the core OS in these bacteria are clustered on the chromosome in the waa (formerly rfa) locus near 81 min on the *E. coli* K-12 and *S. Enterica* linkage maps. Mutations in many of the glycosyl transferases encoded by this locus result in the production of LPS lacking O antigen (termed rough- or R-LPS) since O antigen cannot be ligated to an incomplete lipid A-core acceptor molecule. Strains which produce only R-LPS are more susceptible to complement-mediated serum killing than their wild-type counterparts (reviewed in Whitfield, C., 1994). Mutations in the waa locus which specifically affect the phosphoryl substitution of the core OS heptose region (FIG. 1) can significantly alter outer membrane permeability, giving rise to a pleiotropic phenotype called 'deep rough' (Helander, I. M. et al., 1989; Nikaido, H. 1996). Characteristics of the deep-rough phenotype include the following: 1) hypersensitivity to detergents and hydrophobic antibiotics, 2) sloughing of LPS from the outer membrane, 3) leakage of periplasmic proteins into the culture medium, and 4) a marked decrease in the protein content of the outer membrane (reviewed in Schnaitman, C. A. et al. 1993). The phosphoryl substituents in the heptose region are postulated to be so critical to outer membrane stability because their negative charge allows neighbouring LPS molecules to be crosslinked by divalent cations (Vaara, M. 1992; Nikaido, H. and Vaara, M., 1995).

Previous studies with *S. enterica* serovars Minnesota and Typhimurium (Helander, I. M., et al. 1989), and with *E. coli* K-12 (Parker, C. T., et al. 1992) have implicated waaP in the phosphorylation of both Heptose I ("HepI") and Heptose II ("HepII") (see FIG. 1). Mutation of waaP in these organisms was also reported to cause characteristics of the deep-rough phenotype. Furthermore, in *E. coli* K-12, waaP has been implicated in the addition of HepIII (FIG. 1). Interpretation of these data, however, has been complicated by their reliance on strains with poorly-defined or polar mutations.

The R1 core is the most prevalent among clinical isolates of *E. coli* (Gibb, A. P. et al., 1992) and since its structure is known (Jansson, P. -E., et al. 1981) and the genetics of its outer portion have been resolved (Heinrichs, D. E., et al., 1998), studies were performed using the prototype *E. coli* R1 strain, F470. However, three genes in the waaQ operon of the *E. coli* R1 waa locus (FIG. 2B) have no clearly assigned function: waaQ, P, and Y.

SUMMARY OF THE INVENTION

The present inventors have made precise, non-polar insertion mutations in the waaQ, P, and Y genes of *E. coli* F470, and determined that the enzyme encoded by waaP is responsible for modification of the heptose ("Hep") in the heptose region ("Hep region") by the phosphoryl substitution of the heptose units of the region. The inventors have also identified and isolated highly conserved homologs of the waaP gene from LPS core types R1, R3 and R4 from *E. coli* F470, F653, and F2513, respectively. The inventors have found that the activity of WaaP is to add the phosphoryl substituent to HepI, and that this activity is a prerequisite to the operation of WaaQ and WaaY (both of which are required for the phosphorylation of Hep II). Consequently, the identification and isolation of the waaP gene permits the determination of substances which affect modification of the Hep region, and particularly the modification of Hep I. These substances may be useful in attenuating virulent gram negative pathogens in a host infected by such pathogens.

Accordingly, the present invention provides an isolated nucleic acid molecule containing a sequence encoding the enzyme WaaP which is responsible for modification of the Hep region of LPS by the phosphoryl substitution of the Hep units of the region.

The nucleic acid sequence of waaP is shown in SEQ.ID.NO.:1 (from F470) or SEQ.ID.NO.:3 (from F653) or SEQ.ID.NO.:5 (from F2513). The corresponding amino acid sequence encoded by each one of these nucleic acid sequences of waaP is shown in SEQ.ID.NO.:2 or SEQ.ID.NO.:4 or SEQ.ID.NO.:6, respectively.

Accordingly, in one embodiment of the invention, an isolated nucleic acid molecule is provided having a sequence as shown in SEQ.ID. No.:1 or SEQ.ID.NO.: 3 or SEQ.ID.NO.:5.

Preferably, the purified and isolated nucleic acid molecule comprises (a) a nucleic acid sequence as shown in SEQ. ID. NO.: 1 or SEQ.ID.NO.:3 or SEQ.ID.NO.:5, wherein T can also be U;

(b) nucleic acid sequences complementary to (a);

(c) nucleic acid sequences which are homologous to (a) or (b);

(d) a fragment of (a) to (c) that is at least 15 bases, preferably 20 to 30 bases, and which will hybridize to (a) to (d) under stringent hybridization conditions; or (e) a nucleic acid molecule differing from any of the nucleic acids of (a) to (c) in codon sequences due to the degeneracy of the genetic code.

The invention further includes an isolated protein encoded by a nucleic acid molecule of the invention. Accordingly a preferred embodiment has the amino acid as shown in SEQ. ID. NO. 2 or SEQ.ID.NO.:4 or SEQ.ID.NO.:6.

The invention further provides a method of preventing or treating a gram negative bacterial infection comprising administering an effective amount of a substance that inhibits WaaP to an animal in need thereof.

According to one embodiment, there is provided a method for attenuating virulent gram negative pathogens comprising administering a sufficient amount of an inhibitor of WaaP to attenuate the pathogen. Preferably, the gram negative pathogen is selected from the group of pathogens including *Salmonella enterica, Escherichia coli, Vibrio cholerae, Yersinia enterocolitica, Shigella flexneri, Shigella dysenteriae*, and *Pseudomonas aeruginosa* serotypes 02, 05,16, 18 and 20, *P. aeruginosa* serotypes 03 or 06 and other members of the family Pseudomonadaceae.

Inhibitors of the invention include antibodies which inhibit the activity of the WaaP protein; antibodies which inhibit interaction of the WaaP substrate with the WaaP protein; and antisense oligonucleotide which inhibit translation of the waaP gene.

According to another embodiment, the present invention provides a method of assaying for inhibitors of WaaP, under appropriate conditions, comprising the steps of incubating a gram negative pathogen with a test substance which is suspected of affecting WaaP activity and determining the effect of the substance, preferably phosphorylation of Hep, by comparing to a control. Accordingly, using the methods of the present invention, inhibitors of WaaP in gram negative pathogens will be identified.

According to a further embodiment of the present invention, there is provided a method of treating or preventing a gram negative bacterial infection comprising administering an effective amount of a composition that inhibits WaaP activity, preferably in an animal in need thereof, wherein the composition comprises inhibitors of WaaP activity, preferably in a pharmaceutically acceptable diluent or carrier.

In another embodiment, the present invention provides a vaccine for preventing or treating a gram negative bacterial infection, preferably in an animal in need thereof, comprising an effective amount of a WaaP protein in admixture with a suitable diluent or carrier.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 4 shows the nucleic acid sequence of waaP from *E. coli* F470, representative of the R1 LPS core type (SEQ. I.D. No. 1).

FIG. 5 shows the deduced amino acid sequence from the nucleic acid sequence of FIG. 4 for the WaaP protein of F470 (SEQ. I.D. No. 2).

FIG. 6 shows the nucleic acid sequence of waaP from *E. coli* F653, representative of the R3 LPS core type (SEQ. I.D. No. 3).

FIG. 7 shows the deduced amino acid sequence from the nucleic acid sequence of FIG. 6 for the WaaP protein of F653 (SEQ. I.D. No. 4).

FIG. 8 shows the nucleic acid sequence of the waaP from *E. coli* F2513, representative of the R4 LPS core type (SEQ.I.D. No. 5).

FIG. 9 shows the deduced amino acid sequence from the nucleic acid sequence of FIG. 8 for the WaaP protein of F2513 (SEQ.I.D. No. 6).

DETAILED DESCRIPTION OF THE INVENTION

Figure 1:
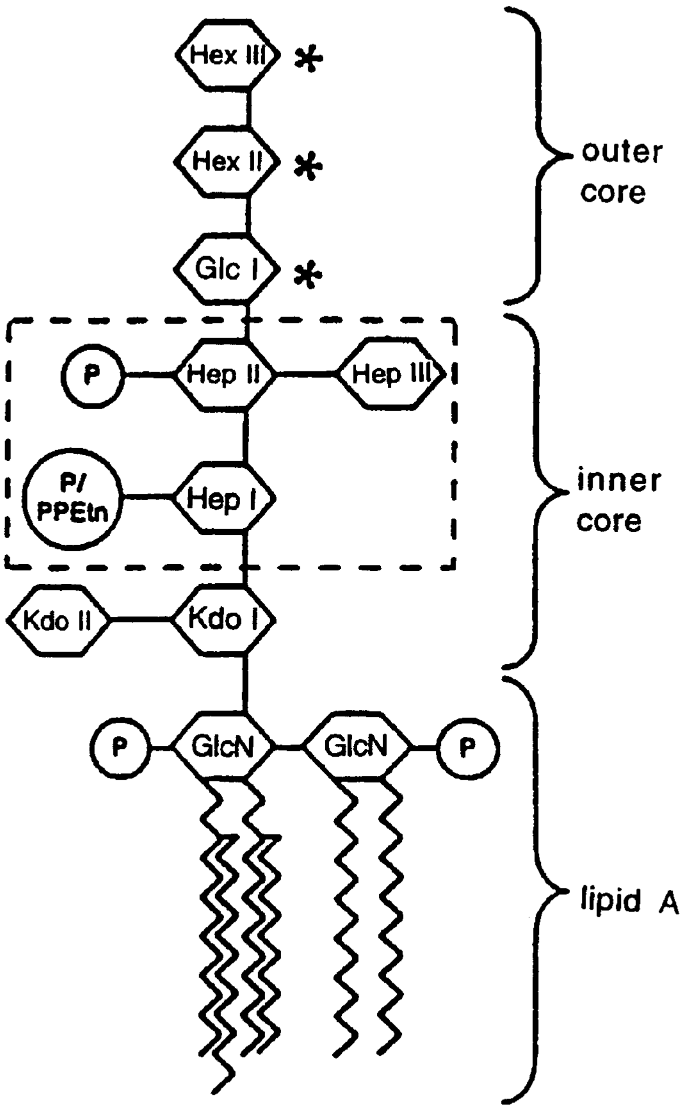
FIG. 1 shows a generalized structure of a lipid A-core portion of a lipopolysaccharide common to *E. coli* and *S. enterica*, highlighting the heptose region.

As mentioned above, the inventors have isolated and characterized the gene (waaP) and its gene product (WaaP) from LPS core types R1, R3 and R4 from *E. coli* F470, F653, and F2513, respectively.

As used in this specification, the term "effective amount" means an amount effective and at dosages and for periods of time necessary to achieve the desired result.

The term "animal" as used herein includes all members of the animal kingdom including mammals, preferably humans.

I. Nucleic Acid Molecules of the Invention

The term "isolated" refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

Broadly stated, the present invention provides an isolated nucleic acid molecule containing a sequence encoding an active protein with the enzyme activity of WaaP. In an embodiment of the invention, an isolated nucleic acid molecule is provided having a sequence as shown in SEQ.ID. No.: 1 or SEQ.ID.NO.:3 or SEQ.ID.NO.:5.

Preferably, the purified and isolated nucleic acid molecule comprises:

(a) a nucleic acid sequence as shown in SEQ. ID. NO.: 1 or SEQ.ID.NO.:3 or SEQ.ID.NO.:5, wherein T can also be U;

(b) nucleic acid sequences complementary to (a);

(c) nucleic acid sequences which are homologous to (a) or (b);

(d) a fragment of (a) to (c) that is at least 15 bases, preferably 20 to 30 bases, and which will hybridize to (a) to (c) under stringent hybridization conditions; or (e) a nucleic acid molecule differing from any of the nucleic acids of (a) to (c) in codon sequences due to the degeneracy of the genetic code.

It will be appreciated that the invention includes nucleic acid molecules encoding truncations of the proteins of the invention, and analogs and homologs of the proteins of the invention and truncations thereof, as described below. It will further be appreciated that variant forms of the nucleic acid molecules of the invention which arise by alternative splicing of an mRNA corresponding to a cDNA of the invention are encompassed by the invention.

Further, it will be appreciated that the invention includes nucleic acid molecules comprising nucleic acid sequences having substantial sequence homology with the nucleic acid sequences as shown in SEQ. ID. NO.: 1 or SEQ.ID.NO.:3 or SEQ.ID.NO.:5 and fragments thereof. The term "sequences having substantial sequence homology" means those nucleic acid sequences which have slight or inconsequential sequence variations from these sequences, i.e., the sequences function in substantially the same manner to produce functionally equivalent proteins. The variations may be attributable to local mutations or structural modifications.

Generally, nucleic acid sequences having substantial homology include nucleic acid sequences having at least 70%, preferably 80–90% identity with the nucleic acid sequence as shown in SEQ. ID. NO.:1 or SEQ.ID.NO.:3 or SEQ.ID.NO.:5.

Another aspect of the invention provides a nucleic acid molecule, and fragments thereof having at least 15 bases, which hybridize to the nucleic acid molecules of the invention under hybridization conditions, preferably stringent hybridization conditions. Appropriate stringency conditions which promote DNA hybridization are known to those skilled in the art, or may be found in Current Protocols in Molecular Biology, John Wiley & Sons, N.Y. (1989), 6.3.1–6.3.6. For example, the following may be employed: 6.0×sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 2.0×SSC at 50° C. In addition, the temperature in the wash step can be at high stringency conditions, at about 65° C.

Isolated and purified nucleic acid molecules having sequences which differ from the nucleic acid sequence shown in SEQ.ID.NO.:1 or SEQ.ID.NO.:3 or SEQ.ID.NO.:5 due to degeneracy in the genetic code are also within the scope of the invention.

Nucleic acid molecules from waaP gene can be isolated by preparing a labelled nucleic acid probe based on all or part of the nucleic acid sequence as shown in SEQ.ID.NO.:1 or SEQ.ID.NO.:3 or SEQ.ID.NO.:5, and using this labelled nucleic acid probe to screen an appropriate DNA library (e.g. a cDNA or genomic DNA library). Nucleic acids isolated by screening of a cDNA or genomic DNA library can be sequenced by standard techniques.

Nucleic acid molecules of the invention can also be isolated by selectively amplifying a nucleic acid using the polymerase chain reaction (PCR) method and cDNA or genomic DNA. It is possible to design synthetic oligonucleotide primers from the nucleic acid molecule as shown in SEQ.ID.NO.:1 or SEQ.ID.NO.:3 or SEQ.ID.NO.:5 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes the WaaP protein. For example, a cDNA can be cloned downstream of a bacteriophage promoter, (e.g., a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The initiation codon and untranslated sequences of the nucleic acid molecules of the invention may be determined using currently available computer software designed for the purpose, such as PC/Gene (IntelliGenetics Inc., Calif.). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The invention also provides nucleic acids encoding fusion proteins comprising a novel protein of the invention and a selected protein, or a selectable marker protein (see below).

Antisense Molecules

Antisense oligonucleotides that are complimentary to a nucleic acid sequence from any one of the waaP genes described herein can also be used in the methods of the present invention to inhibit WaaP activity.

Accordingly, the present invention provides a method of preventing or treating a gram negative bacterial infection comprising administering an effective amount of an antisense oligonucleotide that is complimentary to a nucleic acid sequence from a waaP gene to an animal in need thereof.

Plasmid pWQ909 contains the waaP gene and may be used to develop antisense molecules as described below and to provide protein for the methods and assays described herein.

The term "antisense oligonucleotide" as used herein means a nucleotide sequence that is complimentary to its target.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene (e.g. phosphorothioate derivatives and acridine substituted nucleotides). The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The antisense oligonucleotides may be introduced into tissues or cells using techniques in the art including vectors (retroviral vectors, adenoviral vectors and DNA virus vectors) or physical techniques such as microinjection. The antisense oligonucleotides may be directly administered in vivo or may be used to transfect cells in vitro which are then administered in vivo. In one embodiment, the antisense oligonucleotide may be delivered to macrophages and/or endothelial cells in a liposome formulation.

II. Novel Proteins of the Invention

The invention further includes an isolated protein encoded by nucleic acid molecules of the invention. Within the context of the present invention, a protein of the invention may include various structural forms of the primary protein which retain biological activity.

The term "WaaP" or "WaaP protein" as used herein is intended to include analogs of WaaP, containing one or more amino acid substitutions, insertions, and/or deletions. Amino acid substitutions may be of a conserved or non-conserved nature. Conserved amino acid substitutions involve replacing one or more amino acids with amino acids of similar charge, size, and/or hydrophobicity characteristics. When only conserved substitutions are made the resulting analog should be functionally equivalent to WaaP. Non-conserved substitutions involve replacing one or more amino acids with one or more amino acids which possess dissimilar charge, size, and/or hydrophobicity characteristics.

One or more amino acid insertions may be introduced into the amino acid sequence of WaaP. Amino acid insertions may consist of single amino acid residues or sequential amino acids.

Deletions may consist of the removal of one or more amino acids, or discrete portions (e.g.amino acids) from the WaaP amino acid sequence. The deleted amino acids may or may not be contiguous.

Also included in the expression "WaaP" or "WaaP protein" as used herein are homologs of WaaP. Such homologs are proteins whose amino acid sequences are comprised of the amino acid sequences of WaaP regions from other sources that hybridize under stringent hybridization conditions (which conditions are known to those skilled in the art) with a probe used to obtain WaaP. It is anticipated that a protein comprising an amino acid sequence which is at least 72% preferably 75 to 90% similar, with the amino acid sequence of WaaP will exhibit WaaP activity.

As used herein the expression "WaaP" or "WaaP protein" also contemplates isoforms of the WaaP protein. An isoform contains the same number and kinds of amino acids as WaaP, but the isoform has a different molecular structure. The isoforms contemplated by the present invention are those having the same properties as the protein of the invention as described herein. Also included in the expression are other enzymes that carry out modifications at other positions of Hep and which share similarities to WaaP, such as, for example the WaaY protein.

Broadly stated, the present invention provides an isolated protein with activity equivalent to that of the WaaP protein. As discussed below, WaaP functions like a kinase, and shares similarities with a large number of kinases.

In preferred embodiments of the invention, the protein has the amino acid sequence as shown in SEQ.ID.NO.:2 or SEQ.ID.NO.:4 or SEQ.ID.NO.:6.

In addition to full length amino acid sequences, the proteins of the present invention also include truncations of the protein and analogs and homologs of the protein and truncations thereof as described herein. Truncated proteins may comprise peptides of at least fifteen amino acid residues.

Analogs of the protein having the amino acid sequence shown in SEQ.ID.NO.:2 or SEQ.ID.NO.:4 or SEQ.ID.NO.:6 and/or truncations thereof as described herein, may include, but are not limited to, an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequences shown in SEQ.ID.NO.:2 or SEQ.ID.NO.:4 or SEQ.ID.NO.:6. Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention.

Deletions may consist of the removal of one or more amino acids, or discrete portions from the amino acid sequence shown in SEQ.ID.NO.:2 or SEQ.ID.NO.:4 or SEQ.ID.NO.:6. The deleted amino acids may or may not be contiguous. The lower limit length of the resulting analog with a deletion mutation is about 10 amino acids, preferably 100 amino acids.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequence shown in SEQ.ID.NO.:2 or SEQ.ID.NO.:4 or SEQ.ID.NO.:6 and/or truncations thereof as described herein. Such homologs are proteins whose amino acid sequences are comprised of amino acid sequences that hybridize under stringent hybridization conditions (see discussion of stringent hybridization conditions herein) with a probe used to obtain a protein of the invention. Preferably, homologs of a protein of the invention will have domains containing motifs shared with various kinases, which is characteristic of the protein.

A homologous protein includes a protein with an amino acid sequence having at least 70%, preferably 80–90% identity with the amino acid sequence as shown in SEQ.ID.NO.:2 or SEQ.ID.NO.:4 or SEQ.ID.NO.:6.

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein (see below) to produce fusion proteins. Additionally, immunogenic portions of a protein of the invention are within the scope of the invention.

The proteins of the invention (including truncations, analogs, etc.) may be prepared using recombinant DNA methods. Accordingly, the nucleic acid molecules of the present invention having a sequence which encodes a protein of the invention may be incorporated in a known manner into an appropriate expression vector which ensures good expression of the protein. Possible expression vectors include but are not limited to cosmids, plasmids, or.modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted nucleotide-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990)). Selection of appropriate regulatory sequences is dependent on the host cell chosen, and may be readily accomplished by one of ordinary skill in the art. Examples of such regulatory sequences include the following: a transcriptional promoter and enhancer or RNA polymerase binding sequence, or a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native gene and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence comprising the nucleotides as shown SEQ.ID.NO.:1 or SEQ.ID.NO.:3 or SEQ.ID.NO.:5. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aids in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (199 1).

The proteins of the invention may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

III. Methods of Preventing a Gram Negative Bacterial Infection

As mentioned above, the invention provides a method of preventing or treating a gram negative bacterial infection comprising administering an effective amount of a substance that inhibits WaaP to an animal in need thereof.

The gram negative bacteria may be any bacteria that expresses Waap including *Salmonella enterica Escherichia coli, Vibrio cholerae, Yersinia enterocolitica, Shigella flexneri, Shigella dysenteriae, Pseudomonas aeruginosa* serotypes 02, 05, 16, 18 and 20*, P. aeruginosa* serotypes 03 or 06 and other members of the family Pseudomonadaceae.

The present inventors have made precise, non-polar insertion mutations in the waaQ, P, and Y genes of *E. coli* F470, and determined that the enzyme encoded by waaP is responsible for the phosphorylation of Hep of the Hep region. In particular, it has been found that Hep III is transferred to the Hep region by WaaQ activity and that this is required for phosphorylation of Hep II. Hep II phosphorylation is catalyzed by WaaY. Further, it has been found that Hep I phosphorylation is brought about by WaaP, and that this activity is a prerequisite for the operation of WaaQ and WaaY, and that mutation of waaP such that WaaP activity is antagonized results in no phosphorylation of Hep.

Thus, according to one embodiment the invention provides substances for attenuating a virulent gram negative pathogen, preferably inhibitors of Waap activity, and preferably in an animal in need thereof.

According to another embodiment the invention provides a method of attenuating a virulent gram negative pathogen comprising administering a sufficient amount of an inhibitor of Waap activity to attenuate the pathogen, preferably in an animal in need thereof, preferably in gram negative bacteria, more preferably in *Salmonella enterica Escherichia coli, Vibrio chlolerae, Yersinia enterocolitica, Shigella flexneri, Shigella dysenteriae, Pseudomonas aeruginosa* serotypes 02, 05, 16, 18 and 20,*P. aeruginosa* serotypes 03 or 06 and other members of the family Pseudomonadaceae.

Substances that inhibit the activity of the WaaP protein may be substances that interfere with the WaaP protein (such as antibodies or other protein ligands) or substances that interfere with the expression of the waaP gene such as antisense molecules.

Antibodies

A WaaP protein can be used to prepare antibodies specific for the enzyme. Antibodies can be prepared which bind a distinct epitope in an unconserved region of the protein. An unconserved region of the protein is one which does not have substantial sequence homology to other proteins. Alternatively, a region from a well-characterized domain can be used to prepare an antibody to a conserved region of the WaaP protein. Antibodies having specificity for WaaP may also be raised from fusion proteins.

Conventional methods can be used to prepare antibodies. For example, by using WaaP protein, polyclonal antisera or monoclonal antibodies can be made using standard methods. A mammal, (e.g. a mouse, hamster, or rabbit) can be immunized with an immunogenic form of the polypeptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256, 495–497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77–96), and screening of combinatorial antibody libraries (Huse et al., Science 246, 1275 (1989)]. Hybridoma cells can be screened immunochemically for production of antibodies specifically reactive with the WaaP peptide and the monoclonal antibodies can be isolated. Therefore, the invention also contemplates hybridoma cells secreting monoclonal antibodies with specificity for WaaP protein.

The term "antibody" as used herein is intended to include fragments thereof which also specifically react with WaaP protein. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of the genes of the psb cluster of the invention (See, for example, Morrison et al., Proc. Natl Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with WaaP protein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308–7312 (1983); Kozbor et al., Immunology Today, 4, 7279 (1983); Olsson et al., Meth. Enzymol., 92, 3–16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against WaaP protein may also be generated by screening expression libraries encoding imnunoglobulin genes, or portions thereof, expressed in bacteria with peptides produced from the nucleic acid molecules of the present invention. For example, complete Fab fragments, VH regions and FV regions can be expressed in bacteria using phage expression libraries (See for example Ward et al., Nature 341, 544–546: (1989); Huse et al., Science 246, 1275–1281 (1989); and McCafferty et al. Nature 348, 552–554 (1990)). In an embodiment of the invention, antibodies that bind to an epitope of a protein of the invention are engineered using the procedures described in N. Tout and J. Lam (Clinc. Diagn. Lab. Immunol. Vol. 4(2):147–155, 1997).

The antibodies may be labelled with a detectable marker including various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-111, I123, I125, I131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

The antibodies reactive against WaaP protein may be used to detect a protein of the invention in various samples, for example they may be used in any known immunoassays which rely on the binding interaction between an antigenic determinant of a WaaP protein and the antibodies. Examples of such assays are radioimmunoassays, enzyme immunoassays (e.g. ELISA), immunofluorescence, immunoprecipitation, latex agglutination, hemagglutination, and histochemical tests.

Screening for WaaP Inhibitors

According to an embodiment, of the present invention there is provided a method of assaying for inhibitors of WaaP activity in gram negative pathogens under appropriate conditions comprising the steps of incubating a gram negative pathogen with a test substance which is suspected of affecting WaaP activity and determining the effect of the substance by comparing to a control. WaaP functions like a kinase and accordingly assays for inhibition of kinase activity are within the scope of the present invention. In respect of WaaP, for example, as will be readily understood by those skilled in the art, WaaP can be expressed in a form which may be rapidly purified (such as a His-tagged construct with 6 histidine residues at its N-terminus) using any one of a number of chromatographic methods known to those skilled, such as, for example, metal chelate chromatography in open column or High Performance Liquid Chromatography (HPLC) formats. A purified LPS containing lipid A attached to a phosphate-deficient core oligosaccharide as the acceptor molecule can be extracted from a prototype *E. coli* waaP mutant strain(which has a phosphate-deficient core oligosaccharide) such as, for example strain CWG296. This purification can be conducted by conventional methods. A radio-labelled phosphate of ATP (eg. $^{31}$P-labelled ATP) may be used to provide a phosphodonor in a reaction containing purified WaaP enzyme. Quantification of incorporation of phosphate may be carried out by routine methods such as by separating the LPS from substrate over gel-filtration columns, or by visualization of radiolabel incorporation by separating radiolabeled LPS in sodium dodecyl sulfate gels and exposing the gel to X-ray film. In addition, as is apparent to those skilled in the art, as discussed above under "antibodies", antibodies may be developed which are specific for the phosphorylated heptose that is formed by WaaP thereby allowing for direct detection of enzyme activity in any conventional ELISA format.] As will be appreciated, using the methods of the present invention, inhibitors of Waap activity in gram negative pathogens will be identified. Accordingly, all inhibitors of Waap activity in gram negative pathogens are within the scope of the present invention.

Compositions

The substances identified by the methods described herein, including antisense nucleic acid molecules, and antibodies, may be used for modulating WaaP protein synthesis and activity and accordingly may be used in the treatment of infections caused by gram negative pathogens. The substances identified by the methods described herein, including antisense nucleic acid molecules, and antibodies are preferably used to treat infections caused by bacteria including *Salmonella enterica, Escherichia coli, Vibrio cholerae, Yersinia enterocolitica, Shigella flexneri, Shigella dysenteriae*, and *Pseudomonas aeruginosa* serotypes 02, 05, 16, 18 and 20. The substances etc. are also preferably used to treat infections caused by *P. aeruginosa* serotypes 03 or 06 which are predominant clinical isolates. It will be appreciated that the substances may also be useful to treat infections caused by other members of the family Pseudomonadaceae (eg. *Burkholderia cepacia* and *Burkholderia pseudomallei*).

The substances identified using the methods described herein, including antisense nucleic acid molecules, and antibodies, may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The utility of the substances, antibodies, and compositions of the invention may be confirmed in experimental model systems.

Vaccines

The present invention further includes a vaccine for preventing or treating a gram negative bacterial infection comprising an effective amount of a WaaP protein, preferably in admixture with a suitable diluent or carrier.

Accordingly, the present invention also includes a method of preventing or treating a gram negative bacterial infection comprising administering a vaccine containing an effective amount of a WaaP protein, preferably in admixture with a suitable diluent or carrier, to an animal in need thereof.

The vaccine may include a carrier strain containing a WaaP protein associated with its surface which is effective to provide protection against the bacteria. The carrier strain may selected so that it is incapable of multiplying in vivo. Carrier strains are obtained through selection of variants which occur naturally, or using conventional means known to those skilled in the art. Examples of suitable carrier strains are Shigella species, Salmonella species, *S.typhimurium*, Vibrio species, and Escherichia species.

The vaccine may be a multivalent vaccine and additionally contain immunogens related to other infectious diseases in a prophylactically or therapeutically effective manner. Multivalent vaccines against infectious diseases caused by different infectious agents may contain a carrier strain having amounts of antigens associated with their surfaces which are effective to provide protection against the infectious agents.

The vaccines of the present invention may additionally contain suitable diluents, adjuvants and/or carriers. Preferably, the vaccines contain an adjuvant which can enhance the immunogenicity of the vaccine in vivo. The adjuvant may be selected from many known adjuvants in the art including the lipid-A portion of the LPS from gram negative bacteria (endotoxin), trehalose dimycolate of mycobacteria, the phospholipid lysolecithin, dimethyldictadecyl ammonium bromide (DDA), certain linear polyoxypropylene-polyoxyethylene (POP-POE) block polymers, aluminum hydroxide, and liposomes. The vaccines may also include cytokines that are known to enhance the immune response including GM-CSF, IL-2, IL-12, TNF and IFNγ. The vaccine may also contain preservatives such as sodium azide, thimersol, beta propiolactone, and binary ethyleneimine.

The vaccine compositions of the invention are suitable for administration to subjects in a biologically compatible form in vivo. The expression "biologically compatible form suitable for administration in vivo" as used herein is means a form of the substance to be administered in which any toxic effects are outweighed by the therapeutic effects. The substances may be administered to animals, including mammals, avian species, and fish; preferably humans and various other mammals, including bovines, equines, and swine.

The dose of the vaccine may vary according to factors such as the disease state, age, sex, and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The dose of the vaccine may also be varied to provide optimum preventative dose response depending upon the circumstances.

The vaccines may be administered in a convenient manner such as by injection (subcutaneous, intravenous, intramuscular, etc.), oral administration, inhalation, transdermal administration (such as topical cream or ointment, etc.), or suppository applications.

A vaccine of the invention may contain a nucleic acid molecule encoding a WaaP protein of the invention. In such an embodiment, the WaaP protein is produced in vivo in the host animal. The vaccines containing nucleic acids may be delivered using a suitable vector including retroviral vectors, adenoviral vectors and DNA virus vectors.

A vaccine prepared using the methods described herein may be tested in animal systems in vivo to confirm their efficacy in the prophylaxis or active immunization and treatment of infectious diseases caused by gram negative bacteria and to determine appropriate dosages and routes of administration.

As discussed above, WaaP proteins of the invention are also useful for preparing antibodies which may be used as a means of passive immunization.

The following non-limiting examples are illustrative of the present invention:

EXAMPLES

General Experimental Procedures as Used in the Examples

Bacterial Strains and Growth Conditions—*E. coli* F470 is an R-LPS derivative of an O8:K27 strain (Schmidt, G. et al, 1969), and serves as the prototype for R1 core OS studies. Derivatives of F470 used in this study include CWG296 (F470 with a waaP::aacC1 insertion), CWG297 (F470 with a waaQ::aacC1 insertion), and CWG312 (F470 with a waaY::aacC1 insertion). Bacteria were grown in Luria-Bertani (LB) broth at 37° C. Growth media were supplemented with ampicillin (100 $\mu$g/mL), gentamicin (15 $\mu$g/mL), or chloramphenicol (30 $\mu$g/mL) when necessary.

Figure 2A:
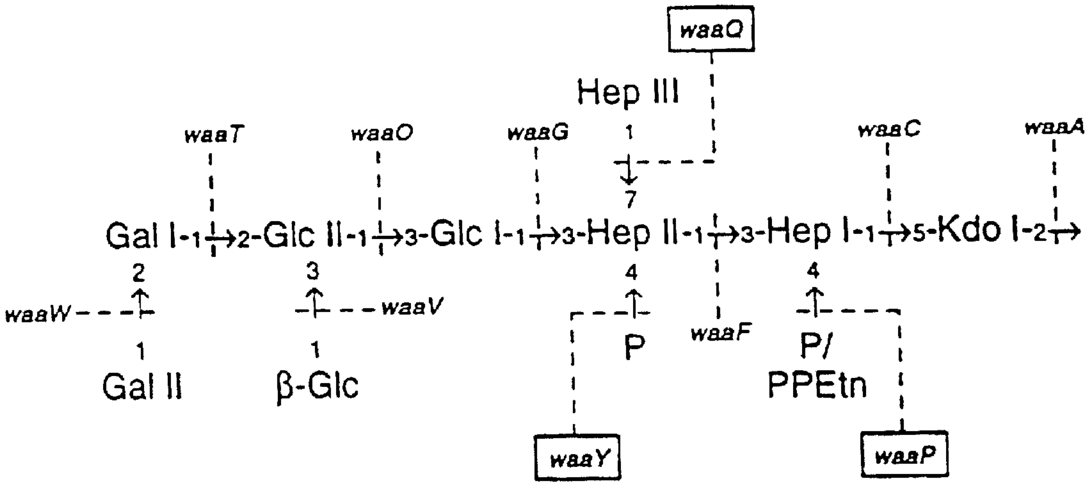
FIG. 2 shows the structure of the R1 core OS of *E. coli* F470, and the genetic organization of the waa locus indicating the locations of the non-polar insertion mutations.
Figure 2B:
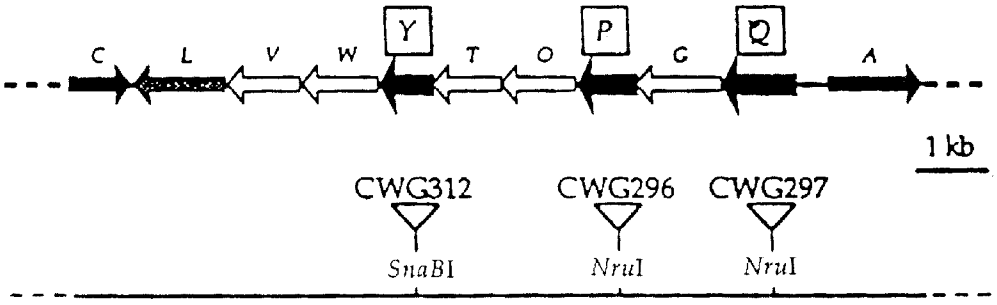

In vitro Mutagenesis and Gene Replacement—The waaY, Q, and P genes of the R1 core OS biosynthesis region were independently mutated by insertion of a non-polar gentamicin-resistance cassette (the aacC1 gene from Tn1696). Briefly, each of the genes (with some flanking DNA) was individually PCR-amplified, cloned into the pBluescript® II SK(+) phagemid (Stratagene), and sequenced to ensure error-free amplification. The aacC1 gene from plasmid pUCGM (Schweizer, H. P., 1993) was then inserted into an appropriate site (near the middle) of the coding region of each gene (FIG. 2B). The DNA fragment containing the insertionally-inactivated gene was subsequently cloned into the suicide delivery vector pMAK705 (Hamilton, C. A. et al., 1989), and chromosomal gene replacement was performed as described previously (Amor, P. A. and Whitfield, C., 1997). Mutations were verified by PCR amplification of the mutated gene from the chromosome and confirmed by sequencing.

DNA Methods—Restriction endonuclease digestion and ligation were performed as described by Sambrook et al. (Sambrook, J. et al., 1989). Restriction enzymes were purchased from either Life Technologies, Inc. (Burlington, Ontario), New England Biolabs (Mississauga, Ontario), or Boehringer Mannheim (Laval, Quebec). Plasmids were introduced into *E. coli* strains by electroporation using a Gene Pulser from Bio-Rad (Mississauga, Ontario). Chromosomal DNA isolation was performed using the Qiagen genomic DNA isolation kit, and plasmid DNA was prepared using QIAprep Miniprep Spin Columns (Qiagen Inc., Santa Clarita, Calif.). When necessary, DNA fragments were isolated from agarose gels using the GENECLEAN® kit from Bio/Can Scientific (Mississauga, Ontario).

PCR and Sequencing Techniques—Oligonucleotides were synthesized using a Perkin-Elmer 394 DNA synthesizer, and sequencing was performed using an ABI 377 DNA sequencing apparatus (Perkin-Elmer, Norwalk, Conn.) in the Guelph Molecular Supercentre at the University of Guelph. PCR amplification was performed using a GeneAmp PCR System 2400 from Perkin-Elmer. The PwoI DNA polymerase enzyme (Boehringer Mannheim) was used as recommended by the manufacturer.

Cloning and Expression of waaP for Complementation—Oligonucleotide primers for the amplification of waaP from the F470 chromosome were designed to introduce appropriate restriction sites for cloning. The forward primer (5'-TGT <u>GGATcc</u>AAATAGTGGGCACTCA-3')(SEQ. I.D. No. 7) introduced a BamHI site (underlined) 32 base pairs downstream of the waaP stop codon, and the complementary reverse primer (5'-GGGTGGTC <u>catATG</u>GTTGAACTTAA-3')(SEQ. I.D. No. 8) introduced an NdeI site (underlined) overlapping the waaP start codon (bases shown in lower case indicate mismatches between the primer and chromosomal sequences). The coding region for waaP alone was subsequently isolated as a BamHI-NdeI fragment, and cloned behind the arabinose-inducible $P_{BAD}$ promoter of the expression vector pBAD18, to generate plasmid pWQ909. L-arabinose was used at a final concentration of 0.002% to induce expression of WaaP from plasmid pWQ909.

Computer Analyses—Homology searches of nucleotide and amino acid sequences in the National Center for Biotechnology Information databases were performed using the BLAST (basic local alignment search tool) or PSI (position-specific iterated)-BLAST server analysis programs (Altschul, S. F. et al., 1990; Altschul, S. F. et al., 1997). Pairwise nucleotide sequence alignments and percent identity scores were obtained using the NALIGN program of the PC/GENE® software package (IntelliGenetics, Inc., Mountain View, Calif.) with an open gap cost of 25 and a unit gap cost of 5. Multiple protein alignments and percentage identity and similarity scores were obtained using the PC/GENE® program CLUSTALV, with an open gap cost of 10 and a unit gap cost of 10. Routine DNA and protein sequence manipulations were performed using the MacVector™ and AssemblyLIGN™ software packages (International Biotechnologies, Inc., New Haven, Conn.).

Sodium dodecyl sulfate (SDS) and Novobiocin Sensitivity Testing—Two-fold serial dilutions of SDS (200→0.1 mg/mL) and novobiocin (200→1.6 $\mu$g/mL) were made in 5 mL volumes of LB. Each series of tubes was point inoculated from an overnight culture of the strain to be tested, and then incubated with shaking at 37° C. Growth was scored as positive if after 8 hours the culture was visibly turbid (i.e. $A_{600}$>0.2).

Preparation of Core OSs—Water-soluble LPSs were obtained by the hot phenol/water extraction of cells (Westphal, O. and Jann, K., 1965), and then treated with 2% acetic acid at 100° C. to cleave the acid-labile ketosidic linkage between the core OS and lipid A. The water-insoluble lipid A was removed by centrifugation (5000×g, 30 min), and the supernatant was passed through a column of BioGel P-2 (1 m×1 cm) with water as eluent. The core-containing fractions were collected and lyophilized.

Sugar Composition and Methylation Linkage Analyses—Sugar composition analysis was performed by the alditol acetate method (Sawardeker, J. H. et al., 1967). Hydrolysis of glycosidic bonds was achieved with 4 M trifluoroacetic acid at 100° C. for 4 h. The samples were then reduced in water with sodium borodeuteride, and acetylated with acetic anhydride using residual sodium acetate as the catalyst. Characterization of the alditol acetate derivatives was performed by gas-liquid chromatography (GLC)-mass spectrometry using a Hewlett-Packard chromatograph equipped with a 30 m DB-17 capillary column (210° C. (30 min) to 240° C. at 2° C./min). Mass spectrometry in the electron impact mode was recorded using a Varian Saturn II mass spectrometer. Linkage data were interpreted based upon the previously published structure of the R1 core (Holst, O. and Brade, H. 1992), as described for analysis of the R1 outer core assembly (Heinrichs, D. E., et al. 1998). Methylation linkage analyses were carried out by the procedure of Ciucanu and Kerek (Ciucanu, I. and Kerek, F., 1984). The permethylated alditol acetate derivatives were fully characterized by GLC-mass spectrometry in the electron impact mode using a column of DB-17 operated isothermally at 190° C. for 60 min.

Fast Atom Bombardment-Mass Spectrometry (FAB-MS)—A fraction of the methylated sample from the linkage analysis was taken for positive ion FAB-MS, which was performed using a Jeol JMS-AX505H mass spectrometer with glycerol/thioglycerol as the matrix, and a tip voltage of 3 kV.

$^{31}$P-NMR Spectroscopy—$^{31}$P-NMR or phosphorus nuclear magnetic resonance spectra were recorded with a Bruker DRX 400 MHz instrument at 161.98 MHz with ortho-phosphoric acid as the external reference (0.0 ppm) and with p1=30 in the proton-decoupling mode. Prior to performing the NMR experiments, the samples were lyophilized three times in $^2H_2O$ (99.9%). The p$^2$H was adjusted with triethylamine when necessary.

Example 1

Structural Analysis of the Core OS From the R1 Prototype Strain, F470—The established structure of the F470 core OS (FIG. 2A) served as a framework for the interpretation of the results. Sugar composition analysis detected the presence of all the expected core OS sugars (glucose, galactose, and heptose, data not shown). Methylation linkage analysis of the core OS from F470 showed all of the permethylated alditol acetate derivatives from the outer core residues in the ratios expected (FIG. 3A and Table I). No peaks were observed in the GLC chromatogram (FIG. 3A) for the derivatives from either HepI or HepII because the phosphoryl substituents attached to these residues (FIG. 2A) made their derivatives too polar to elute from the column. This proved useful in subsequent analyses because it allowed the loss of phosphoryl substituents from HepI and HepII to be monitored as the appearance of either a 3-substituted or 3,7-disubstituted heptose derivative peak in the GLC chromatogram.

$^{31}$P-NMR spectroscopy of the F470 core OS at p$^2$H 8.5 yielded the spectrum shown in FIG. 3E. The signal at 5 ppm is indicative of a phosphomonoester (phosphate ("P") on either HepI or HepII), while the two peaks near −10 ppm are characteristic of a diphosphodiester (2-aminoethyldiphosphate ("PPEtN") on HepI (Hep=L-glycero-10 D-manno-heptose)) (Helander, I. M. et al., 1994). At lower solvent p$^2$H values, the peak at 5 ppm was shifted upfield (data not shown), confirming its assignment as a phosphomonoester (Helander, I. M. et al., 1994). The ratio of P to PPEtN in the F470 core OS was estimated by the relative peak heights in FIG. 3E. As expected, there was more P than PPEtN, since HepII is only substituted with P while HepI is either substituted with P or PPEtN.

Example 2

Sequence Analysis and Mutagenesis of waaY—Pairwise nucleotide alignments of the waaY coding region from *E. coli* K-12, R1, R2, and R4, and *S. enterica* serovar Typhimurium (all of the core types for which DNA sequence of the waa loci was available) showed identities ranging from 59.4–99.0%. Multiple alignment of the predicted WaaY proteins showed high total similarity (85.3%) but much lower identity (43.1%). In BLASTP searches of the available databases, WaaY showed no significant homologies to other characterized proteins. However, using the PSI-BLAST server analysis program, queries with the various WaaY protein sequences suggested biologically relevant similarities to a large number of kinases (data not shown). This circumstantial data suggested a potential role for WaaY in phosphorylation reactions.

To test this possibility, strain CWG312 was derived by insertion of the aacC1 gene into the unique SnaBI site in the waaY coding region of F470 (FIG. 2B). The LPS from the resulting mutant migrated similarly to that of the F470 parent in sodium dodexyl sulphate-polyacrylamine gel electrophoresis (SDS-PAGE) (data not shown), precluding any significant effect of the mutation on core OS extension. However, the minimum inhibitory concentration (MIC) of SDS and of novobiocin for CWG312 were slightly less than for F470 (Table II), suggesting subtle changes in outer membrane properties.

Example 3

Structural Analysis of the CWG312 core OS and Assignment of WaaY Function—The structure of the deduced CWG312 core OS is shown in Table I. Sugar composition analysis detected the presence of all the core OS sugars found in F470 (data not shown). Linkage analysis of CWG312 resulted in a GLC chromatogram that was identical to that from the F470 parent (compare FIGS. 3A and B) except for the appearance of a peak (peak 9, FIG. 3B) corresponding to a 3,7-disubstituted heptose derivative (Table I). Based on the F470 structure, this derivative must result from unphosphorylated HepII. $^{31}$P-NMR spectroscopy further corroborated the loss of P from the CWG312 core OS: in the F470 parent there was more P than PPEtN, but in CWG312 there was slightly more PPEtN than P (compare FIGS. 3E and F). The observed shift in the ratio of P to PPEtN is explained by the loss of P from HepII, leaving only P and PPEtN on HepI. Therefore, given the disappearance of P from HepII in the CWG312 core OS and the biologically significant sequence similarity of WaaY to some kinases, WaaY is concluded to be involved in the phosphorylation of HepII.

Example 4

Sequence Analysis and Mutagenesis of waaQ—In *E. coli* K-12, R1, R2, and R4, and in *S. enterica* serovar Typhimurium, waaQ is the first gene of the central operon of the core OS biosynthesis region (FIG. 2B). Pairwise nucleotide alignments of the waaQ genes from these core types showed identities ranging from 68.5–98.6%. Multiple sequence alignment of the predicted WaaQ proteins reflected the homology observed at the nucleotide level with a total similarity of 88.1% (64.0% identity). The predicted WaaQ proteins showed limited homology to both WaaC (40.6% total similarity, 10.8% identity) and WaaF (50.1% total similarity, 16.5% identity), the HepI (Kadrmas, J. L. and Raetz, C. R., 1998) and HepII transferases, respectively (FIG. 2A).

Strain CWG297 was derived by insertion of the aacC1 gene into the unique NruI site in the waaQ coding region of F470 (FIG. 2B). The LPS from the resulting mutant migrated similarly to that of the F470 parent in SDS-PAGE (data not shown), but the MIC of SDS and of novobiocin for CWG297 were slightly less than for F470 (Table II) and comparable with the values for the waaY mutant, CWG312.

Example 5

Structural Analysis of the CWG297 Core OS and Assignment of WaaQ Function—Sugar composition analysis detected the presence of all the core OS sugars found in F470 (data not shown). The structure of the CWG297 core OS shown in Table I was deduced from methylation linkage analysis and $^{31}$P-NMR spectroscopy as follows. Firstly, methylation linkage analysis of the CWG297 core OS showed all of the outer core derivatives in the expected ratios (Table I), but the terminal heptose derivative (resulting from HepIII) was completely absent (note the absence of peak 6 in FIG. 3C). The disappearance of the HepIII side branch was also confirmed by FAB-MS (data not shown). Given the similarity of WaaQ to WaaC and WaaF (the HepI and HepII transferases respectively, FIG. 2A) and the complete absence of HepIII in the CWG297 core OS, it was concluded that waaQ encodes the transferase for the branch HepIII residue. Interestingly, the appearance of a 3-linked heptose derivative in the linkage analysis of CWG297 (peak 8, FIG. 3C) also indicated the loss of a phosphoryl substituent from either HepI or HepI (both are 3-linked after the loss of HepIII) due to the waaQ mutation. To resolve which heptose residue was lacking its phosphoryl substituent, the $^{31}$P-NMR spectrum of the CWG297 core OS was compared to the spectra from F470 and CWG312 (waaY). Given the similar P to PPEtN ratios for CWG297 and CWG312 (compare FIGS. 3F and G) it was concluded that the same phosphoryl substituent (P on HepII) was absent in both strains. If the waaQ mutation had affected phosphoryl substitution of HepI, the ratio of P relative to PPEtN would have increased rather than decreased. The observed loss of P from HepII in CWG297 did not contradict the assignment of WaaQ as the HepIII transferase since WaaY had already been assigned as the enzyme responsible for the phosphorylation of HepII (see above). Rather, the transfer of HepIII by WaaQ appears to be a prerequisite to the phosphorylation of HepII catalyzed by WaaY.

Example 6

Sequence Analysis and Mutagenesis of waaP—In *E. coli* K-12, R1, R2, and R4, and in *S. enterica* serovar Typhimurium, waaP occurs as the third gene of the central operon of the core OS biosynthesis region (FIG. 2B). Pairwise nucleotide alignments indicated that the waaP gene from these core types was highly conserved (71.8–98.1% identity). Similarity at the protein level was even higher, with multiple sequence alignment of the predicted WaaP proteins showing a total similarity of 93.3%, and 75.9% identity. In BLASTP searches of the available databases, WaaP showed no significant similarity to other characterized proteins, as previously reported (Schnaitman, C. A. and Klena, J. D., 1993; Parker, C. T. et al., 1992). However, the recently developed PSI-BLAST server analysis program again identified biologically relevant similarities shared between the various WaaP proteins and a large number of kinases (data not shown). In experiments based on information about catalytic bases in kinases in the public domain, (i.e., site-directed mutagenesis and crystallography data from protein kinases in other organisms[2,3]) we mutated an amino acid predicted to function as the enzyme's catalytic base. Using a PCR-based site-directed mutagenesis protocol,(see General Methods herein) we mutated aspartate (D) 162 to an alanine (A) residue on plasmid pWQ909[4], which contains w a a P cloned behind an arabinose-inducible promoter. Plasmid pWQ909 and pWQ909(D162A) were then electroporated into our defined *E. coli* waaP mutant strain to determine their ability to complement its deep-rough phenotype. The results (not shown) clearly indicate that aspartate 162 is an essential residue, and support our proposal that WaaP functions like a kinase.]

Strain CWG296 was derived by insertion of the aacC1 gene into the unique NruI site in the waaP coding region of F470 (FIG. 2B). The resulting mutant was hypersensitive to novobiocin and SDS (Table II), as expected based on results from previous studies (Helander, I. M. et al., 1989; Parker, C. T. et al., 1992). Introduction of multicopy waaP (on plasmid pWQ909) into CWG296 restored wild-type levels of resistance to these hydrophobic agents (Table II).

Example 7

Structural Analysis of the CWG296 Core OS and Assignment of WaaP Function—Sugar composition analysis detected the presence of all the core OS sugars found in F470 (data not shown). The structure of the CWG296 core OS shown in Table I was deduced from methylation linkage analysis and $^{31}$P-NMR spectroscopy as follows. Firstly, $^{31}$P-NMR spectroscopy showed a complete lack of phosphorus in the CWG296 core OS (FIG. 3H), indicating that mutation of waaP resulted in the loss of all phosphoryl substituents from HepI and HepII. The GLC chromatograms from the CWG296 and F470 methylation linkage analyses were then compared to determine any other effects of the waaP mutation on the core OS structure. Of note, the terminal heptose derivative from HepIII was almost completely absent in the CWG296 core OS (note the absence of peak 6 in FIG. 3D). This lack of terminal heptose was also observed by FAB-MS (data not shown), and implicated the waaP mutation in the loss of HepIII in addition to the above-mentioned deficiency in phosphoryl substituents. The absence of phosphoryl substituents and of HepIII was further corroborated by the appearance of a large peak in the CWG296 GLC chromatogram (peak 8, FIG. 3D) corresponding to a substituted heptose derivative from HepI and HepII. The calculated molar ratio of this derivative (Table I) was somewhat lower than expected, but the observed signal was clearly twice that from CWG297 (compare peak 8 in FIGS. 3C and D, and Table I), as expected based on their predicted structures. (The prolonged retention time of the 3-substituted heptose derivative on the GLC column may account for this slight discrepancy in molar ratios.) Finally, the amounts of terminal glucose (from the β-Glc side branch) and of 2,3-disubstituted glucose (from GlcII where Glc=D-Glucose) were noticeably decreased in CWG296 (compare peaks 1 and 7 in FIG. 3A and D, and see Table I). The decrease in 2,3-disubstituted glucose was offset by the appearance of an approximately equal amount of 2-substituted glucose (note the appearance of peak 3, FIG. 3D), reflecting GlcII lacking the β-Glc substitution.

In summary, the mutation of waaP resulted in a core OS which was devoid of all phosphoryl substituents and the branch HepIII residue, and which appeared to contain a lower percentage of β-Glc substituted GlcII. Since WaaY and WaaQ had already been assigned in this study as the enzymes responsible for the phosphorylation of HepII and the transfer of HepIII respectively (see above), and since WaaV had been previously assigned as the β-Glc transferase (see FIG. 2A, and Heinrichs, D. E. et al., 1998), it is concluded that the enzyme encoded by waaP is responsible for the phosphoryl substitution of HepI. This conclusion is supported by the sequence similarity of WaaP to known kinases, first reported in this study. The loss of other substituents and sugar residues from the CWG296 core OS does not contradict this assignment, but suggests that the activity of WaaP is a prerequisite to the efficient functioning of other enzymes.

Discussion

The data presented here identify WaaY as the enzyme which phosphorylates HepII, WaaQ as the transferase for the branch HepIII residue, and WaaP as the enzyme responsible for the addition of either P or PPEtN to HepI. With these assignments, a function has now been ascribed to every gene in the waaQ operon of the core OS biosynthesis region in the *E. coli* R1 prototype strain, F470 (see FIG. 2A). Moreover, the deduced structures of the core OSs from the waaY, Q, and P mutants are consistent with a sequence of events in the decoration of the heptose region of the core OS where 1) WaaP adds P or PPEtN to HepI; 2) WaaQ adds HepIII to HepII; and 3) WaaY adds P to HepII.

The conclusion that the activity of WaaP is a prerequisite to the functioning of both WaaQ and WaaY is based on the fact that the core OS of CWG296 (waaP) does not have HepIII or a P substituent on HepII (Table I) even though functional copies of the waaQ and waaY genes are present on the chromosome. Likewise, the activity of WaaQ is concluded to be required prior to the functioning of WaaY because the core OS of CWG297 (waaQ) does not have the P substituent on HepII (Table I) even though the waaY gene in this mutant is fully functional. These results can be explained by a fastidious substrate requirement in each sequential reaction, such that WaaQ can only effect the transfer of HepII to a lipid A-core acceptor with P or PPEtN on HepI, and WaaY can only phosphorylate HepII if the lipid A-core acceptor has both HepIII and a phosphoryl substituent on HepI. Alternatively, these data could reflect a requirement for specific protein-protein interactions to provide a functional multi-enzyme complex.

The data presented here provide an explanation for the multiple functions attributed to waaP in the literature. For example, the suggested involvement of WaaP in the transfer of HepII in *E. coli* K-12 (Parker, C. T. et al., 1992) has now been resolved: WaaQ is the HepIII transferase, but requires the prior functioning of WaaP. It had previously been suggested, based solely on limited predicted protein sequence similarities, that the product of waaQ might encode the HepIII transferase (Schnaitman, C. A. and Klena, J. D., 1993). This study provides the first genetic and structural data to support this claim. Another reported effect of waaP mutations in *S. enterica* serovars Minnesota and Typhimurium (Helander, I. M. et al., 1989) is a truncation of the core OS distal to GlcI (FIG. 1); however, the precisely defined, non-polar waaP mutations derived in this study clearly show that core extension is complete, although there is a reduction in the efficiency of branch β-Glc substitution. The core truncation observed in the 'waaP' mutants of *S. enterica* could be explained by polar or multiple mutations which eliminate the function of downstream genes.

The contribution of the heptose region phosphoryl substituents to outer membrane stability is clearly shown by novobiocin and SDS sensitivity testing, as illustrated in Table II. The lack of P on HepII in CWG312 (waaY) and in CWG297(waaQ) resulted in a minor increase in the sensitivity of these strains to the hydrophobic agents. However, the complete lack of phosphoryl substituents in the core OS of CWG296 (waaP) resulted in a 32-fold increase in the susceptibility to novobiocin, and more than a 1000-fold increase in the susceptibility to SDS. Therefore, only the complete loss of phosphoryl substituents from the heptose region of the core was sufficient to cause the characteristic hypersensitivity to hydrophobic agents associated with the deep-rough phenotype. It is noteworthy that the negative charges required for LPS crosslinking need not come from phosphoryl substituents: for example, the core OS of Klebsiella pneumoniae is devoid of phosphate, but contains negatively-charged galacturonic acid residues instead (S üisskind, M. et al., 1995; Severn, W. B. et al., 1996).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

Vaara, M. (1992) Microbiol. Rev. 56, 395–411.

Whitfield, C., Amor, P. A., and Köplin, R. (1997) Mol. Microbiol. 23, 629–638.

Raetz, C. R. H. (1996) in *Escherichia coli* and Salmonella. Cellular and Molecular Biology (Neidhardt, F. C., Curtiss III, R., Ingraham, J. L., Lin, E. C. C., Low, K. B., Magasanik, B., Reznikoff, W. S., Riley, M., Schaechter, M., and Umbarger, H. E., eds) Vol. 1, pp. 1035–1063, ASM Press, Washington, D.C.

Holst, O., and Brade, H. (1992) in Bacterial Endotoxic Lipopolysaccharides (Morrison, D. C., and Ryan, J. L., eds) Vol. 1, pp. 134–170, CRC Press, Boca Raton, Fla.

Olsthoorn, M. M. A., Petersen, B. O., Schlecht, S., Haverkamp, J., Bock, K., Thomas-Oates, J. E., and Holst, O. (1998) J. Biol. Chem. 273, 3817–3829.

Whitfield, C., Keenleyside, W. J., and Clarke, B. R. (1994) in *Escherichia coli* in domestic animals and man. (Gyles, C. L., ed), pp. 437–494, CAB International.

Helander, I. M., Vaara, M., Sukupolvi, S., Rhen, M., Saarela, S., Zahringer, U., and Mäkelä, P. H. (1989) Eur. J. Biochem. 185, 541–546.

Nikaido, H. (1996) in *Escherichia coli* and Salmonella. Cellular and Molecular Biology. (Neidhardt, F. C., Curtiss III, R., Ingraham, J. L., Lin, E. C. C., Low, K. B., Magasanik, B., Reznikoff, W. S., Riley, M., Schaechter, M., and Umbarger, H. E., eds) Vol. 1, pp. 29–47, ASM Press, Washington, D.C.

Schnaitman, C. A., and Klena, J. D. (1993) Microbiol. Rev. 57, 655–682.

Nikaido, H., and Vaara, M. (1985) Microbiol. Rev. 49, 1–32.

Dröge, W., Ruschmann, E., Ljideritz, O., and Westphal, O. (1968) Eur. J. Biochem. 4, 134–138.

Mühlradt, P., Risse, H. J., Lüderitz, O., and Westphal, O. (1968) Eur. J. Biochem. 4, 139–145.

Parker, C. T., Kloser, A. W., Schnaitman, C. A., Stein, M. A., Gottesman, S., and Gibson, B. W. (1992) J. Bacteriol. 174, 2525–2538.

Gibb, A. P., Barclay, G. R., Poxton, I. R., and di Padova, F. (1992) J. Infect. Dis. 166, 1051–1057.

Jansson, P.-E., Lindberg, A. A., Lindberg, B., and Wollin, R. (1981) Eur. J. Biochem. 115, 571–577.

Heinrichs, D. E., Yethon, J. A., and Whitfield, C. (1998) submitted.

Schmidt, G., Jann, B., and Jann, K. (1969) Eur. J. Biochem. 10, 501–510.

Schweizer, H. P. (1993) BioTechniques 15, 831–833.

Hamilton, C. A., Aldea, M., Washburn, B. K., Babtizke, P., and Kushner, S. R. (1989) J. Bacteriol. 171, 4617–4622.

Amor, P. A., and Whitfield, C. (1997) Mol. Microbiol. 26, 145–161.

Sambrook, J., Fritsch, E. F., and Maniatis, T. (1989) Molecular Cloning: A Laboratory Manual. 2nd edition., Cold Spring Harbor Laboratory, Cold Spring Harbor, New York.

Guzman, L.-M., Belin, D., Carson, M. J., and Beckwith, J. (1995) J. Bacteriol. 177, 4121–4130.

Altschul, S. F., Gish, W., Miller, W., Myers, E. W., and Lipman, D. J. (1990) J. Mol. Biol. 215, 403–410.

Altschul, S. F., Madden, T. L., Schäffer, A. A., Zhang, J., Zhang, Z., Miller, W., and Lipman, D. J. (1997) Nucl. Acids Res. 25(17), 3389–3402.

Westphal, O., and Jann, K. (1965) Meth. Carbohydr. Chem. 5, 83–91.

Sawardeker, J. H., Sloneker, J. H., and Jeanes, A. (1967) Anal. Chem. 39, 1602–1604.

Ciucanu, I., and Kerek, F. (1984) Carbohydr. Res. 131, 209–217.

Helander, I. M., Kilpeläinen, I., and Vaara, M. (1994) Mol. Microbiol. 11, 481–487.

Kadrmas, J. L., and Raetz, C. R. (1998) J. Biol. Chem. 273, 2799–2807.

Sirisena, D. M., MacLachlan, P. R., Liu, S.-L., Hessel, A., and Sanderson, K. E. (1994) J. Bacteriol. 176, 2379–2385.

Brabetz, W., Müller-Loennies, S., Holst, O., and Brade, H. (1997) Eur. J. Biochem. 247, 716–724.

Parker, C. T., Pradel, E., and Schnaitman, C. A. (1992) J. Bacteriol. 174, 930–934.

Südsskind, M., Müller-Leonnies, S., Nimmich, W., Brade, H., and Hoist, O. (1995) Carbohydr. Res. 269, C1–C7.

Severn, W. B., Kelly, R. F., Richards, J. C., and Whitfield, C. (1996) J. Bacteriol. 178, 1731–1741.

DETAILED LEGENDS FOR VARIOUS FIGURES

FIG. 1. Generalized structure of the lipid A-core portion of lipopolysaccharide common to *E. coli* and *S. enterica*, highlighting the heptose region. Core residues are designated by sugar abbreviation and number to facilitate identification. The abbreviations are as follows: GlcN, D-glucosamine; P, phosphate; Kdo, 3-deoxy-D-manno-oct-2-ulosonic acid; Hep, L-glycero-D-manno-heptose; PPEtN, 2-aminoethyl diphosphate; Glc, D-glucose; Hex, D-hexose (either glucose or galactose). *, structural differences between the five *E. coli* and two *S. enterica* core types are due to differences between the HexII and HexIII sugars, and to the nature and positions of side-branch substitutions of GlcI, HexII, and HexIII.

FIG. 2. Structure of the R1 core OS of *E. coli* F470, and genetic organization of the waa locus indicating the locations of the non-polar insertion mutations. A, structure of the core OS isolated from acetic acid-hydrolyzed F470 LPS (mild acid hydrolysis cleaves both the KdoI-26'-lipid A and KdoII-24-KdoI linkages). All sugars are in the pyranose configuration and the linkages are α unless otherwise indicated. The data which identify the genetic determinants for the modification of the heptose region (enclosed in boxes) are reported in this study. The assignment of function to other genes has been reported previously (Heinrichs, D. E. et al., 1998; Kadrmas, J. L. and Raetz, C. R., 1998; Brabetz, W., et al., 1997). B, map of the R1 core OS biosynthesis region (waa locus) indicating the insertion site for the aacC1 gene cassette (represented by an open triangle) in each of the F470 derivatives. The CWG*** designations for each derivative strain are indicated above the triangles. Only the restriction endonuclease sites used for mutagenesis are shown. The waaF gene (encoding the HepII transferase) lies just upstream of waaC in both *E. coli* K-12 and *S. enterica* serovar Typhimurium, but sequence data for this region in *E. coli* R1 is not currently available.

Figure 3:
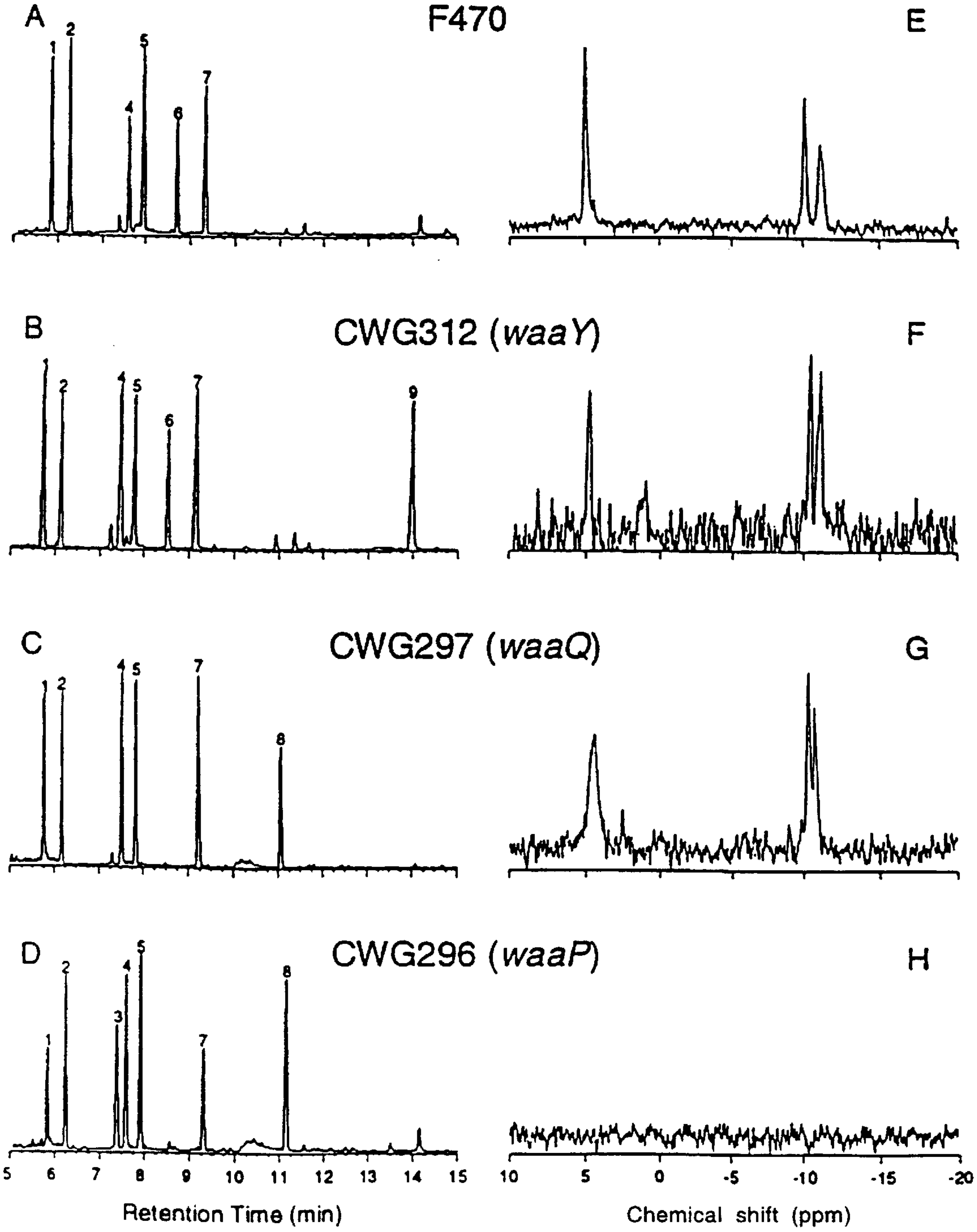
FIG. 3 illustrates the methylation linkage analyses and $^{31}$P-NMR spectroscopy of the core OSs from F470 and derivatives.

FIG. 3. Methylation linkage analyses and $^{31}$P-NMR spectroscopy of the core OSs from F470 and derivatives. A-D, GLC chromatograms from the methylation linkage analyses of A, F470; B, CWG312; C, CWG297; and D, CWG296. The numbered peaks correspond to the permethylated alditol acetate derivatives from 1) terminal Glc (5.8 min); 2) terminal Gal (6.2 min); 3) 2-substituted Glc (7.3 min); 4) 3-substituted Glc (7.5 min); 5) 2-substituted Gal (7.8 min); 6) terminal Hep (8.6 min); 7) 2,3-disubstituted Glc (9.2 min); 8) 3-substituted Hep (11.0 min); and 9) 3,7-disubstituted Hep (14.0 min). The approximate molar ratios of these derivatives are shown in Table I. E-H, $^{31}$P-NMR spectra of the core OSs from E, F470; F, CWG312; G, CWG297; and H, CWG296. The signal at 5 ppm is indicative of a phosphomonoester (P on either HepI or HepII), and the two peaks near −10 ppm are characteristic of a diphosphodiester (PPEtN on HepI) (Helander, I. M. et al., 1994).

TABLE I

Structures of the core OSs from F470 and derivatives as deduced from linkage analyses
The peaks in the GLC chromatograms from the linkage analyses (FIG. 3A–D) were correlated to the substituted sugar residues from which they were derived. Approximate molar ratios were calculated from the integrated peak areas. The published structure of the F470 core OS (FIG. 2A) was used as a framework for the interpretation of results as discussed in the text.

| Strain | Peak | Linkage | Approximate Molar Ratio | Core OS Structure |
|---|---|---|---|---|
| F470 (parent) | 1 | Glc-(1→ | 1.0 | |
| | 2 | Gal-(1→ | 1.0 | |
| | 4 | →3)-Glc-(1→ | 0.7 | |
| | 5 | →2)-Gal-(1→ | 1.3 | |
| | 6 | Hep-(1→ | 0.6 | |
| | 7 | →2,3)-Glc-(1→ | 1.0 | |

Hep III
1
↓
7
Gal I-1→2-Glc II-1→3-Glc I-1→3-Hep II-1→3-Hep I-1→
2 3 4 4
↑ ↑ ↑ ↑
1 1 P P/PPEtN
Gal II β-Glc

TABLE I-continued

Structures of the core OSs from F470 and derivatives as deduced from linkage analyses
The peaks in the GLC chromatograms from the linkage analyses (FIG. 3A–D) were correlated to the substituted sugar residues from which they were derived. Approximate molar ratios were calculated from the integrated peak areas. The published structure of the F470 core OS (FIG. 2A) was used as a framework for the interpretation of results as discussed in the text.

| Strain | Peak | Linkage | Approximate Molar Ratio | Core OS Structure |
|---|---|---|---|---|
| CWG312 | 1 | Glc-(1→ | 0.9 | Hep III |
| (waaY) | 2 | Gal-(1→ | 0.8 | 1 |
| | 4 | →3)-Glc-(1→ | 1.1 | ↓ |
| | 5 | →2)-Gal-(1→ | 1.0 | 7 |
| | 6 | Hep-(1→ | 0.7 | Gal I-1→2-Glc II-1→3-Glc I-1→3-Hep II-1→3-Hep I-1→ |
| | 7 | →2,3)-Glc-(1→ | 1.1 | 2 3 4 |
| | 9 | →3,7)-Hep-(1→ | 1.1 | ↑ ↑ ↑ |
| | | | | 1 1 P/PPEtN |
| | | | | Gal II β-Glc |
| CWG297 | 1 | Glc-(1→ | 0.9 | Gal I-1→2-Glc II-1→3-Glc I-1→3-Hep II-1→3-Hep I-1→ |
| (waaQ) | 2 | Gal-(1→ | 1.0 | 2 3 4 |
| | 4 | →3)-Glc-(1→ | 1.1 | ↑ ↑ ↑ |
| | 5 | →2)-Gal-(1→ | 1.0 | 1 1 P/PPEtN |
| | 7 | →2,3)-Glc-(1→ | 1.1 | Gal II β-Glc |
| | 8 | →3)-Hep-(1→ | 0.7 | |
| CWG296 | 1 | Glc-(1→ | 0.5 | Gal I-1→2-Glc II-1→3-Glc I-1→3-Hep II-1→3-Hep I-1→ |
| (waaP) | 2 | Gal-(1→ | 0.9 | 2 3 |
| | 3 | →2)-Glc-(1→ | 0.7 | ↑ ↑ |
| | 4 | →3)-Glc-(1→ | 1.0 | 1 1 |
| | 5 | →2)-Gal-(1→ | 1.1 | Gal II β-Glc[a] |
| | 7 | →2,3)-Glc-(1→ | 0.6 | |
| | 8 | →3)-Hep-(1→ | 1.1 | |

[a]in CWG296, the β-Glc residue is only present in about 50% of the core OSs.

TABLE II

Minimum inhibitory concentration (MIC) of SDS and novobiocin for F470 and derivatives.

| | MIC | |
|---|---|---|
| Strain | SDS (mg/mL) | novobiocin (μg/mL) |
| F470 (parent) | >200 | 200 |
| CWG312 (waaY) | 200 | 100 |
| CWG297 (waaQ) | 200 | 100 |
| CWG296 (waaP) | 0.1 | 6.3 |
| CWG296 (waaP) + pWQ909 | 200 | 100 |

We claim:

1. An isolated nucleic acid molecule comprising a nucleic acid sequence selected from the group consisting of SEQ ID NO: 1, SEQ ID NO: 3, and SEQ ID NO: 5.

2. An isolated nucleic acid molecule comprising:

(a) a nucleic acid sequence selected from the group, consisting of SEQ ID NO: 1, SEQ ID NO: 3, and SEQ ID NO: 5, wherein the sequences can comprise either T or U;

(b) nucleic acid sequences fully complementary to (a); or (c) a nucleic acid molecule differing from any of the nucleic acids of (a) to (b) in codon sequences due to the degeneracy of the genetic code.

* * * * *

SEQUENCE LISTING

```
<160> NUMBER OF SEQ ID NOS: 8

<210> SEQ ID NO 1
<211> LENGTH: 795
<212> TYPE: DNA
<213> ORGANISM: E.coli
```

-continued

<400> SEQUENCE: 1

```
atggttgaac ttaaagagcc gtttgccacg ttatggcgcg gcaaagatcc ttttgaggaa     60
gttaaaacct tgcagggtga ggtatttcgt gaactggaaa ctcgccgtac tctgcgcttt    120
gaaatggcgg gcaaaagcta ttttctcaaa tggcatcgcg gcacgaccct gaaagagata    180
atcaaaaatt tactctcatt gcggatgcca gtattaggcg ctgaccgcga atggaatgcg    240
attcatcgac tgcgggatgt cggcgttgat actatgtatg gggtggcatt tggcgaaaaa    300
ggcatgaatc cgctgaccag aacttcattt attattaccg aagatctgac accaaccata    360
agtctggaag attactgtgc tgactgggcg actaaccctc cagatgttcg cgtaaagcgt    420
atgcttatta agcgtgtcgc gacgatggtg cgcgatatgc atgctgcggg cattaaccac    480
cgtgactgtt atatctgtca tttcctgctg cacttgcctt tttccggtaa ggaagaggag    540
ttaaaaattt cggtaattga cctgcaccgg gcgcagcttc gcacgcgcgt tccacgtcgt    600
tggcgggata aagatcttat tggcctttat ttttcttcga tgaatatcgg cctgactcag    660
cgggatatct ggcggtttat gaaagtgtat tttgccgccc cgcttaaaga cattctcaag    720
caggaacaag gactgctgtc gcaagcagaa gcaaaagcca caaaaatcag ggaaagaacg    780
attcgaaaat cgttg                                                      795
```

<210> SEQ ID NO 2
<211> LENGTH: 265
<212> TYPE: PRT
<213> ORGANISM: E.coli

<400> SEQUENCE: 2

```
Met Val Glu Leu Lys Glu Pro Phe Ala Thr Leu Trp Arg Gly Lys Asp
  1               5                  10                  15

Pro Phe Glu Glu Val Lys Thr Leu Gln Gly Glu Val Phe Arg Glu Leu
             20                  25                  30

Glu Thr Arg Arg Thr Leu Arg Phe Glu Met Ala Gly Lys Ser Tyr Phe
         35                  40                  45

Leu Lys Trp His Arg Gly Thr Thr Leu Lys Glu Ile Ile Lys Asn Leu
     50                  55                  60

Leu Ser Leu Arg Met Pro Val Leu Gly Ala Asp Arg Glu Trp Asn Ala
 65                  70                  75                  80

Ile His Arg Leu Arg Asp Val Gly Val Asp Thr Met Tyr Gly Val Ala
                 85                  90                  95

Phe Gly Glu Lys Gly Met Asn Pro Leu Thr Arg Thr Ser Phe Ile Ile
            100                 105                 110

Thr Glu Asp Leu Thr Pro Thr Ile Ser Leu Glu Asp Tyr Cys Ala Asp
        115                 120                 125

Trp Ala Thr Asn Pro Pro Asp Val Arg Val Lys Arg Met Leu Ile Lys
    130                 135                 140

Arg Val Ala Thr Met Val Arg Asp Met His Ala Ala Gly Ile Asn His
145                 150                 155                 160

Arg Asp Cys Tyr Ile Cys His Phe Leu Leu His Leu Pro Phe Ser Gly
                165                 170                 175

Lys Glu Glu Glu Leu Lys Ile Ser Val Ile Asp Leu His Arg Ala Gln
            180                 185                 190

Leu Arg Thr Arg Val Pro Arg Arg Trp Arg Asp Lys Asp Leu Ile Gly
        195                 200                 205

Leu Tyr Phe Ser Ser Met Asn Ile Gly Leu Thr Gln Arg Asp Ile Trp
    210                 215                 220
```

-continued

```
Arg Phe Met Lys Val Tyr Phe Ala Ala Pro Leu Lys Asp Ile Leu Lys
225                 230                 235                 240

Gln Glu Gln Gly Leu Leu Ser Gln Ala Glu Ala Lys Ala Thr Lys Ile
                245                 250                 255

Arg Glu Arg Thr Ile Arg Lys Ser Leu
            260                 265


<210> SEQ ID NO 3
<211> LENGTH: 795
<212> TYPE: DNA
<213> ORGANISM: E.coli

<400> SEQUENCE: 3

atggttgaac ttaaagagcc gtttgccacg ttatggcgcg gcaaagatcc ttttgaggaa     60

gttaaaacct tgcagggtga ggtatttcgt gaactggaaa ctcgccgtac tctgcgcttt    120

gaaatggcgg gcaaaagcta ttttctcaaa tggcatcgcg gcacgaccct gaaagagata    180

atcaaaaatt tactctcatt gcggatgcca gtattaggcg ctgaccgcga atggaatgcg    240

attcatcgac tgcgggatgt cggcgttgat actatgtatg ggtggcatt tggcgaaaaa     300

ggcatgaatc cgctgaccag aacttcattt attattaccg aagatctgac accaaccata    360

agtcttgaag attacagtgc tgactgggcg actaaccctc cagatgttcg cgtaaagcgt    420

atgcttatta agcgtgtcgc gacgatggtg cgcgatatgc atgctgcggg cattaaccac    480

cgtgactgtt atatctgtca tttcctgctg cacttgcctt tttccggtaa ggaagaggag    540

ttaaaaattt cggtaattga cctgcaccgg gcgcagcttc gcacgcgcgt tccacgtcgt    600

tggcgggata aagatcttat tggctttat ttttcttcga tgaatatcgg cctgactcag     660

cgggatatct ggcggtttat gaaagtgtat tttgccgccc cgcttaaaga cattctcaag    720

caggaacaag gactgctgtc gcaagcagaa gcaaaagcca caaaaatcag ggaaagaacg    780

attcgaaaat cgttg                                                      795


<210> SEQ ID NO 4
<211> LENGTH: 265
<212> TYPE: PRT
<213> ORGANISM: E.coli

<400> SEQUENCE: 4

Met Val Glu Leu Lys Glu Pro Phe Ala Thr Leu Trp Arg Gly Lys Asp
  1               5                  10                  15

Pro Phe Glu Glu Val Lys Thr Leu Gln Gly Glu Val Phe Arg Glu Leu
             20                  25                  30

Glu Thr Arg Arg Thr Leu Arg Phe Glu Met Ala Gly Lys Ser Tyr Phe
         35                  40                  45

Leu Lys Trp His Arg Gly Thr Thr Leu Lys Glu Ile Ile Lys Asn Leu
     50                  55                  60

Leu Ser Leu Arg Met Pro Val Leu Gly Ala Asp Arg Glu Trp Asn Ala
 65                  70                  75                  80

Ile His Arg Leu Arg Asp Val Gly Val Asp Thr Met Tyr Gly Val Ala
                 85                  90                  95

Phe Gly Glu Lys Gly Met Asn Pro Leu Thr Arg Thr Ser Phe Ile Ile
            100                 105                 110

Thr Glu Asp Leu Thr Pro Thr Ile Ser Leu Glu Asp Tyr Ser Ala Asp
        115                 120                 125

Trp Ala Thr Asn Pro Pro Asp Val Arg Val Lys Arg Met Leu Ile Lys
```

-continued

```
    130                 135                 140

Arg Val Ala Thr Met Val Arg Asp Met His Ala Ala Gly Ile Asn His
145                 150                 155                 160

Arg Asp Cys Tyr Ile Cys His Phe Leu Leu His Leu Pro Phe Ser Gly
                165                 170                 175

Lys Glu Glu Glu Leu Lys Ile Ser Val Ile Asp Leu His Arg Ala Gln
            180                 185                 190

Leu Arg Thr Arg Val Pro Arg Arg Trp Arg Asp Lys Asp Leu Ile Gly
        195                 200                 205

Leu Tyr Phe Ser Ser Met Asn Ile Gly Leu Thr Gln Arg Asp Ile Trp
    210                 215                 220

Arg Phe Met Lys Val Tyr Phe Ala Ala Pro Leu Lys Asp Ile Leu Lys
225                 230                 235                 240

Gln Glu Gln Gly Leu Leu Ser Gln Ala Glu Ala Lys Ala Thr Lys Ile
                245                 250                 255

Arg Glu Arg Thr Ile Arg Lys Ser Leu
            260                 265


<210> SEQ ID NO 5
<211> LENGTH: 795
<212> TYPE: DNA
<213> ORGANISM: E.coli

<400> SEQUENCE: 5

atggttgaac ttaaagagcc gtttgccacg ttatggcgcg gtaaagatcc ttttgaggaa      60

gttaaaacct tgcagggtga ggtatttcgt gaactggaaa ctcgccgcac tctgcgcttt     120

gaaatggcgg gcaaaagcta ttttctcaaa tggcatcgcg gcacgaccct gaaagagata     180

atcaaaaatt tactctcatt gcggatgcca gtattaggcg cagaccgcga atggaatgcg     240

attcatcgac tgcgggatgt cggcgttgat actatgtatg ggtggcatt cggcgaaaaa     300

ggcattaatc cgctcaccag aacctcgttt attataaccg aagatctgac accaaccatc     360

agtctggaag attactgtgc tgactgggcg actaacccac cagatgttcg cgtaaagcgt     420

atgcttatta agcgtgtcgc gacgatggtg cgcgatatgc atgctgcggg cattaaccac     480

cgcgactgtt atatctgtca tttcctgcta cacttgcctt tttccggtaa ggaagaggag     540

ttaaaaattt cggtaattga cctgcaccgg gcgcagcttc gcacgcgcgt tccacgtcgt     600

tggcgcgata aagatcttat tggcctttat ttttcttcga tgaatatcgg cctgactcag     660

cgggatatct ggcggtttat gaaagtgtat tttgccgccc cgcttaaaga cattctcaag     720

caggaacaag gactgctgtc gcaagcagaa gaaaaagcca caaaaatcag ggaaagaacg     780

attcgaaaat cgttg                                                      795


<210> SEQ ID NO 6
<211> LENGTH: 265
<212> TYPE: PRT
<213> ORGANISM: E.coli

<400> SEQUENCE: 6

Met Val Glu Leu Lys Glu Pro Phe Ala Thr Leu Trp Arg Gly Lys Asp
  1               5                  10                  15

Pro Phe Glu Glu Val Lys Thr Leu Gln Gly Glu Val Phe Arg Glu Leu
             20                  25                  30

Glu Thr Arg Arg Thr Leu Arg Phe Glu Met Ala Gly Lys Ser Tyr Phe
         35                  40                  45
```

-continued

```
Leu Lys Trp His Arg Gly Thr Thr Leu Lys Glu Ile Ile Lys Asn Leu
     50                  55                  60

Leu Ser Leu Arg Met Pro Val Leu Gly Ala Asp Arg Glu Trp Asn Ala
 65                  70                  75                  80

Ile His Arg Leu Arg Asp Val Gly Val Asp Thr Met Tyr Gly Val Ala
                 85                  90                  95

Phe Gly Glu Lys Gly Ile Asn Pro Leu Thr Arg Thr Ser Phe Ile Ile
            100                 105                 110

Thr Glu Asp Leu Thr Pro Thr Ile Ser Leu Glu Asp Tyr Cys Ala Asp
        115                 120                 125

Trp Ala Thr Asn Pro Pro Asp Val Arg Val Lys Arg Met Leu Ile Lys
    130                 135                 140

Arg Val Ala Thr Met Val Arg Asp Met His Ala Ala Gly Ile Asn His
145                 150                 155                 160

Arg Asp Cys Tyr Ile Cys His Phe Leu Leu His Leu Pro Phe Ser Gly
                165                 170                 175

Lys Glu Glu Glu Leu Lys Ile Ser Val Ile Asp Leu His Arg Ala Gln
            180                 185                 190

Leu Arg Thr Arg Val Pro Arg Arg Trp Arg Asp Lys Asp Leu Ile Gly
        195                 200                 205

Leu Tyr Phe Ser Ser Met Asn Ile Gly Leu Thr Gln Arg Asp Ile Trp
    210                 215                 220

Arg Phe Met Lys Val Tyr Phe Ala Ala Pro Leu Lys Asp Ile Leu Lys
225                 230                 235                 240

Gln Glu Gln Gly Leu Leu Ser Gln Ala Glu Glu Lys Ala Thr Lys Ile
                245                 250                 255

Arg Glu Arg Thr Ile Arg Lys Ser Leu
            260                 265


<210> SEQ ID NO 7
<211> LENGTH: 25
<212> TYPE: DNA
<213> ORGANISM: E.coli

<400> SEQUENCE: 7

tgtggatcca aatagtgggc actca                                           25


<210> SEQ ID NO 8
<211> LENGTH: 25
<212> TYPE: DNA
<213> ORGANISM: E.coli

<400> SEQUENCE: 8

gggtggtcca tatggttgaa cttaa                                           25
```